(12) United States Patent
Perbost

(10) Patent No.: US 6,171,797 B1
(45) Date of Patent: Jan. 9, 2001

(54) METHODS OF MAKING POLYMERIC ARRAYS

(75) Inventor: Michel G. M. Perbost, Cupertino, CA (US)

(73) Assignee: Agilent Technologies Inc., Palo Alto, CA (US)

(*) Notice: Under 35 U.S.C. 154(b), the term of this patent shall be extended for 0 days.

(21) Appl. No.: 09/421,952

(22) Filed: Oct. 20, 1999

(51) Int. Cl.[7] .............. C12Q 1/38; C12P 19/34; C07H 21/02; C07H 21/04
(52) U.S. Cl. ............... 435/6; 435/91.2; 435/6; 536/23.1; 536/24.3
(58) Field of Search ............... 435/6, 91.2; 536/23.1, 536/24.3

(56) References Cited

U.S. PATENT DOCUMENTS

| | | |
|---|---|---|
| 5,242,974 | 9/1993 | Holmes . |
| 5,384,261 | 1/1995 | Winkler et al. . |
| 5,405,783 | 4/1995 | Pirrung et al. . |
| 5,412,087 | 5/1995 | McGall et al. . |
| 5,424,186 | 6/1995 | Fodor et al. . |
| 5,429,807 | 7/1995 | Matson et al. . |
| 5,436,327 | 7/1995 | Southern et al. . |
| 5,445,934 | 8/1995 | Fodor et al. . |
| 5,472,672 | 12/1995 | Brennan . |
| 5,527,681 | 6/1996 | Holmes . |
| 5,529,756 | 6/1996 | Brennan . |
| 5,545,531 | 8/1996 | Rava et al. . |
| 5,554,501 | 9/1996 | Coassin et al. . |
| 5,556,752 | 9/1996 | Lockhart et al. . |
| 5,561,071 | 10/1996 | Hollenberg et al. . |
| 5,580,697 | * 12/1996 | Keana et al. .............. 435/6 |
| 5,599,695 | 2/1997 | Pease et al. . |
| 5,624,711 | 4/1997 | Sundberg et al. . |
| 5,639,603 | 6/1997 | Dower et al. . |
| 5,658,734 | 8/1997 | Brock et al. . |

FOREIGN PATENT DOCUMENTS

| | | |
|---|---|---|
| 0 742 287 A2 | 11/1996 | (EP) . |
| 0 799 897 A1 | 10/1997 | (EP) . |
| 93/17126 | 9/1993 | (WO) . |
| 95/11995 | 5/1995 | (WO) . |
| WO 95/25116 * | 9/1995 | (WO) .............. C07H/21/00 |
| 95/35505 | 12/1995 | (WO) . |
| 97/14706 | 4/1997 | (WO) . |
| 98/30575 | 7/1998 | (WO) . |

OTHER PUBLICATIONS

"Large Scale Oligonucleotide Synthesis," Oct. 28–29, 1997 at Westin Horton Plaza Hotel, San Diego, California.

\* cited by examiner

*Primary Examiner*—John S. Brusca
*Assistant Examiner*—Keffrey S. Lundgren
(74) *Attorney, Agent, or Firm*—Gordon Stewart

(57) ABSTRACT

Methods are provided for making arrays of distinct polymers covalently bonded to the surface of the a solid support. In the subject methods, at least two distinct polymers, e.g. nucleic acids, are contacted with the surface of a solid support under conditions sufficient for the nucleic acids to become covalently bonded to the surface of the solid support through a cycloaddition reaction, e.g. through the reaction of a diene with a dienophile. Also provided are arrays produced by the subject methods, kits comprising the same and methods for using the arrays in analyte detection, e.g. hybridization, assays.

32 Claims, 2 Drawing Sheets

METHODS OF MAKING POLYMERIC ARRAYS

INTRODUCTION

1. Technical Field

The field of this invention is nucleic acid arrays.

2. Background of the Invention

"Biochips" or arrays of binding agents, such as oligonucleotides and peptides, have become an increasingly important tool in the biotechnology industry and related fields. These binding agent arrays, in which a plurality of binding agents are deposited onto a solid support surface in the form of an array or pattern, find use in a variety of applications, including gene expression analysis, drug screening, nucleic acid sequencing, mutation analysis, and the like.

A critical feature of many arrays that have been developed is that each of the polymeric compounds of the array is stably attached to a discrete location on the array surface, such that its position remains constant and known through the use of the array. Stable attachment is achieved in a number of different ways, including covalent bonding of the polymer to the support surface and non-covalently interaction of the polymer with the surface. In many embodiments, it is desirable to covalently attach the binding agent to the surface of the solid support. A number of different protocols have been developed to provide for covalent attachment of binding agents, such as oligonucleotides, to a support surface, e.g. cross-linking of polymers to the surface, growing polymers from a support surface via stepwise reactions, and the like.

However, despite the number of different protocols that have been developed to date, there is continued interest in the development of new covalent attachment protocols. Of particular interest is the development of new protocols for producing nucleic acid arrays.

Relevant Literature

Patents and patent applications describing arrays of biopolymeric compounds and methods for their fabrication include: U.S. Pat. Nos. 5,242,974; 5,384,261; 5,405,783; 5,412,087; 5,424,186; 5,429,807; 5,436,327; 5,445,934; 5,472,672; 5,527,681; 5,529,756; 5,545,531; 5,554,501; 5,556,752; 5,561,071; 5,599,695; 5,624,711; 5,639,603; 5,658,734; WO 93/17126; WO 95/11995; WO 95/35505; EP 742 287; and EP 799 897. Also of interest are WO 97/14706 and WO 98/30575.

SUMMARY OF THE INVENTION

Methods and devices for producing arrays of binding agents covalently attached to the surface of a solid support are provided. In the subject methods, at least two distinct polymers of differing monomeric unit sequence are covalently attached to different locations on the surface of a solid support through a cycloaddition reaction, e.g. through the reaction of a diene with a dienophile. As such, the resultant arrays are characterized in that the polymers are attached to the solid support via a linking group that includes a cycloadduct. The subject methods are particularly suited for use in the preparation of nucleic acid arrays.

DEFINITIONS

Figure 1:
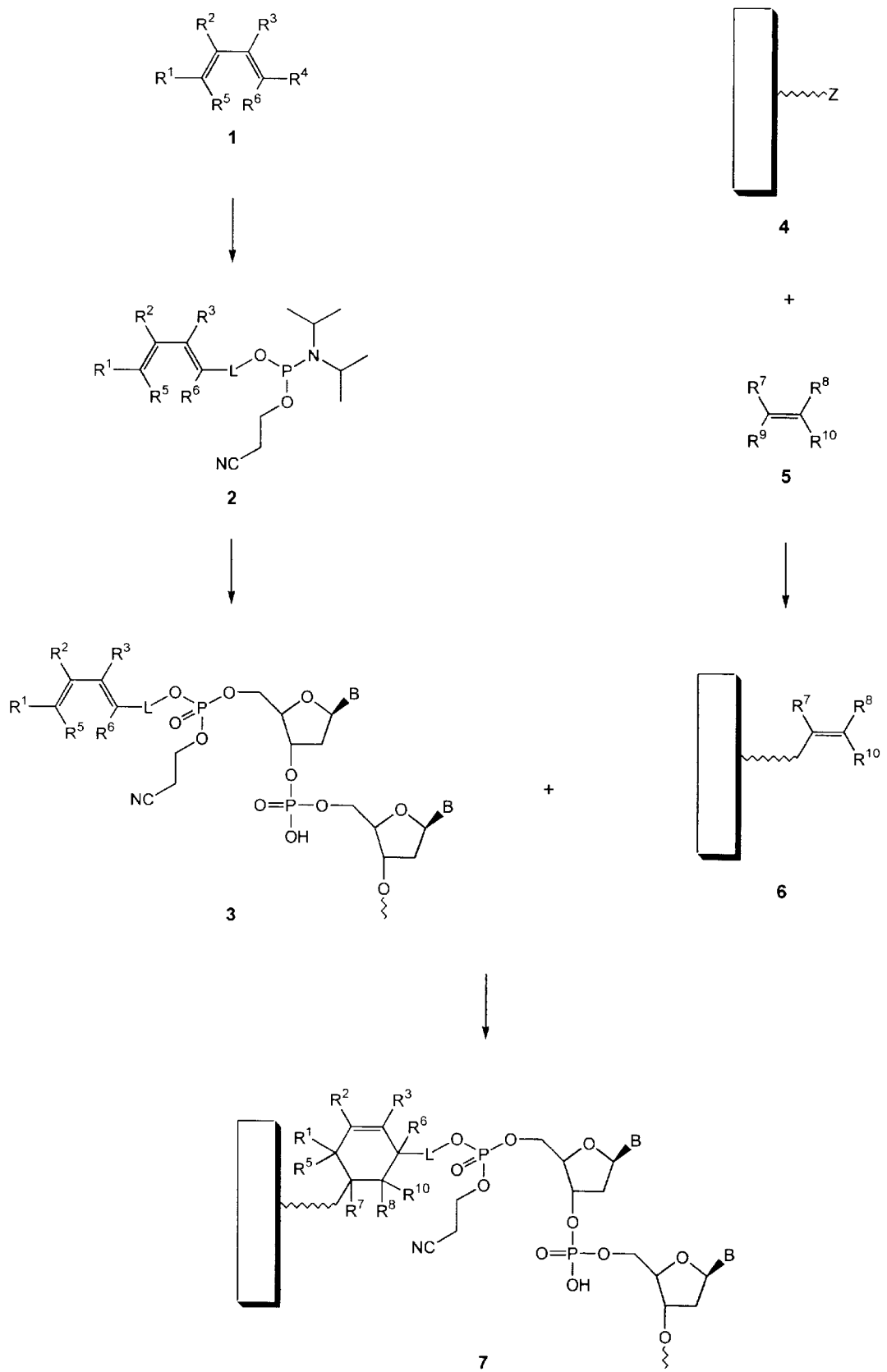
FIG. 1 provides a reaction scheme for the covalent attachment of an oligonucleotide to a substrate surface according to an embodiment of the subject invention.
Figure 2A:
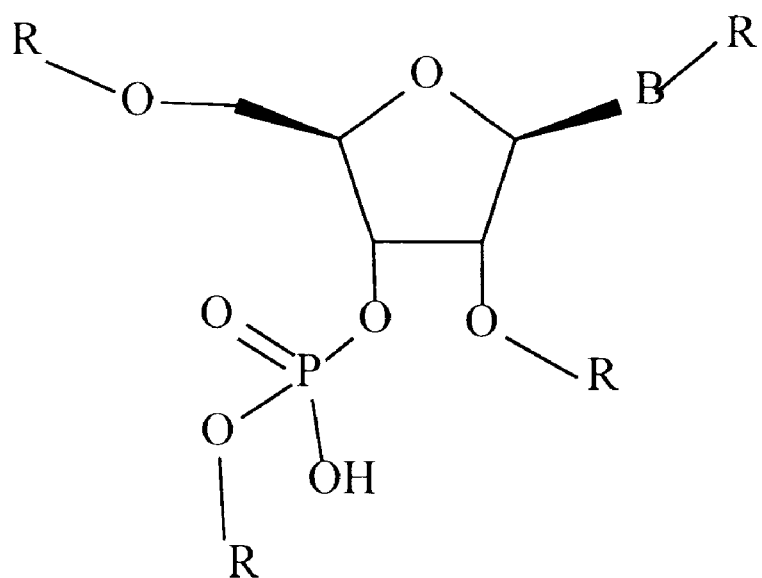
FIG. 2A provides a depiction of the different locations of a nucleotide that a cycloaddition reactive moiety may be attached and FIG. 2B provides a depiction of a substrate having either a diene or a dienophile reactive moiety displayed on its surface.
Figure 2B:
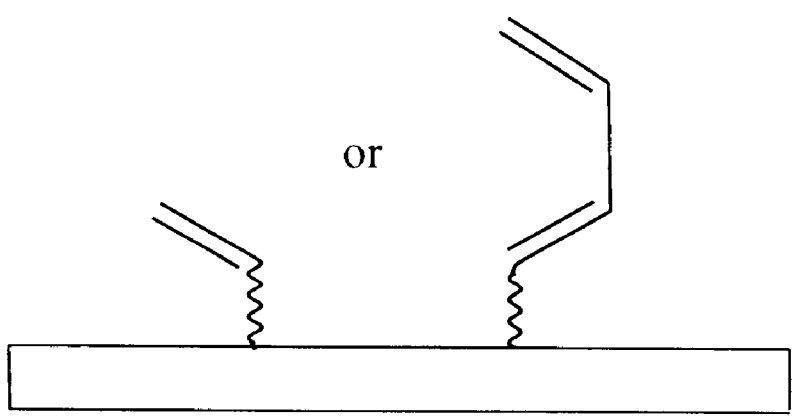

The term "polymer" means any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

The term "peptide" as used herein refers to any compound produced by amide formation between a carboxyl group of one amino acid and an amino group of another group.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues.

The term "nucleic acid" as used herein means a polymer composed of nucleotides, e.g. deoxyribonucleotides or ribonucleotides, or compounds produced synthetically (e.g. PNA as described in U.S. Pat. No. 5,948,902 and the references cited therein) which can hybridize with naturally occurring nucleic acids in a sequence specific manner analogous to that of two naturally occurring nucleic acids.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length.

The term "polynucleotide" as used herein refers to single or double stranded polymer composed of nucleotide monomers of generally greater than 100 nucleotides in length.

DESCRIPTION OF THE SPECIFIC EMBODIMENTS

Methods for producing arrays of polymers covalently attached to the surface of a solid support, as well as the arrays produced thereby, are provided. In the subject methods, at least two or more distinct polymers of different monomeric unit sequence are covalently attached to the surface of the solid support through a cycloaddition reaction, e.g. through the reaction of a diene with a dienophile. The resultant arrays are characterized in that the polymers are covalently attached to the surface of the solid support through a linking group that includes a cycloadduct, e.g. a six membered ring. Also provided are methods of using the subject arrays in analyte detection assays and kits comprising the subject arrays.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Methods

As summarized above, the subject invention provides a method for producing arrays of polymers covalently bound to the surface of a solid support. A critical aspect of the subject invention is that the polymers are contacted with the surface of the solid support under conditions such that a cycloaddition reaction occurs between cycloaddition reactive groups present on the polymers and on the surface of the solid support. More specifically, a critical step of the subject methods is that at least two distinct polymers are contacted with the surface of the solid support under cycloaddition conditions, such that the polymers become bound to the surface of the support through a linkage group characterized by the presence of a cycloadduct, e.g. a six membered ring. Thus, the polymers and the substrate surface are contacted under conditions in which the cycloaddition reactive groups present on the substrate surface and the polymers react with each other to produce a cycloadduct between each polymer and the substrate surface.

In the broadest sense, any convenient cycloaddition reaction that is compatible with the polymers and other components of the array may be employed in the subject methods. Cycloaddition reactions of interest include, but are not limited to, [4+2], [3+2] and [2+2] cycloaddition reactions, where such reaction are known to those of skill in the art. See Carruthers, *Cycloaddition Reactions in Organic Synthesis*, Pergamon Press, Oxford (1990). In many embodiments, the cycloaddition reaction that is employed for attachment of the polymers to the surface is a [4+2] cycloaddition reaction, i.e. a Diels-Alder reaction. In such embodiments of the subject invention, the cycloaddition reactive moieties present on the polymers and the substrate surface are generally selected from the group consisting of dienes and a dienophiles.

In fabricating polymeric arrays according to the subject methods, a surface of a solid support or substrate that has been modified to display a first cycloaddition reactive moiety is contacted under cycloaddition reaction conditions to two or more distinct polymers (usually two or more distinct polymeric compositions that include multiple copies of the same polymer), where each distinct polymer includes a second cycloaddition reactive moiety at some position, generally at either termini. The first and second cycloaddition reactive moieties or groups are selected such that they participate in a cycloaddition reaction to produce a cycloadduct under conditions in which the substrate and polymer are contacted.

Solid Supports

The subject methods may be used to fabricate polymeric arrays on a variety of different solid supports or substrates, including both flexible and rigid substrates. By flexible is meant that the support is capable of being bent, folded or similarly manipulated without breakage. Examples of solid materials which are flexible solid supports with respect to the present invention include membranes, flexible plastic films, and the like. By rigid is meant that the support is solid and does not readily bend, i.e. the support is not flexible. As such, rigid substrates are sufficient to provide physical support and structure to the nucleic acid spots present thereon. Furthermore, when the rigid supports of the subject invention are bent, they are prone to breakage.

The substrates may take a variety of configurations ranging from simple to complex. Thus, the substrate could have an overall slide or plate configuration, such as a rectangular, square or disc configuration. In many embodiments, the substrate will have a rectangular cross-sectional shape, having a length of from about 4 mm to 200 mm, usually from about 4 to 150 mm and more usually from about 4 to 125 mm and a width of from about 4 mm to 200 mm, usually from about 4 mm to 120 mm and more usually from about 4 mm to 80 mm, and a thickness of from about 0.01 mm to 5.0 mm, usually from about 0.1 mm to 2 mm and more usually from about 0.2 to 1 mm.

The substrates may be fabricated from a variety of materials. In certain embodiments, e.g. where one is interested in the production of nucleic acid arrays for use in research and related applications, the materials from which the substrate may be fabricated should ideally exhibit a low level of non-specific binding during hybridization events. In many situations, it will also be preferable to employ a material that is transparent to visible and/or UV light. For flexible substrates, materials of interest include: nylon, nitrocellulose, polypropylene, polyester films, such as polyethylene terephthalate, and the like, where a nylon membrane, as well as derivatives thereof, is of particular interest in this embodiment. For rigid substrates, specific materials of interest include: silicon; glass; plastics, e.g. polytetrafluoroethylene, polypropylene, polystyrene, polycarbonate, and blends thereof, and the like; metals, e.g. gold, platinum, and the like; etc.

The substrate surface may be smooth or substantially planar, or have irregularities, such as depressions or elevations, or have a porous surface, such as is found in porous glass or silica. The surface may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, conformal silica or glass coatings, polymers, small organic molecules and the like. Polymeric layers of interest include layers of: peptides, proteins, polynucleic acids or mimetics thereof, e.g. peptide nucleic acids and the like; polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto, e.g. conjugated.

A critical feature of the substrates or solid supports is that at least one surface of the substrate, i.e. that surface to which the polymers are to be covalently bound during the subject methods, comprises a first reactive group, i.e. a cycloaddition reactive group, capable of reacting with a second group present on the polymers in a cycloaddition reaction to produce a covalent linkage between the polymer and the substrate surface, where the covalent linkage is characterized by the presence of a cycloadduct or ring structure, usually a six membered ring. The cycloaddition reactive group present on the substrate surface, e.g. the diene, dienophile, etc., may be present at one or more distinct locations on the substrate surface, usually at a plurality of distinct locations on the substrate surface, where in many embodiments the surface will uniformly display the cycloaddition reactive group, i.e. the cycloaddition reactive group will be uniformly or evenly distributed across the surface of the substrate such that there are no gaps or spaces on the surface in which the group is not displayed. As discussed in greater detail below, the cycloaddition reactive group may be a number of different groups, and will generally be a diene or a dienophile in many embodiments of the invention. In many embodiments, the critical angle of the surface displaying the cycloaddition reactive group is sufficient to provide for extremely low drop spreading of fluid deposited on the substrate surface, where in many embodiments the contact angle ranges from about 20 to 100, usually from about 40 to 100 and more usually from about 60 to 100°.

In general, the substrate surfaces that are employed in the subject methods may be represented by the following formula:

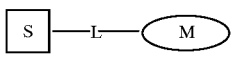

where

M is a cycloaddition reactive moiety, e.g. a diene or a dienophile;

S is substrate and

L is a bond or linking group.

As mentioned above, M is generally a diene or a dienophile in many embodiments of the subject invention, e.g. in those embodiments where the cycloaddition reaction is a Diels-Alder reaction. Diene moieties that may present on the subject substrate surfaces are groups containing two conjugated double bonds, which can undergo a [4+2] cycloaddition reaction with a dienophile. The atoms forming the double bonds can be carbon or a heteroatom, e.g. N, S, O, etc. The diene group or moiety may be substituted or unsubstituted. Typically, the diene is a substituted alkene of the formula:

wherein $R^1$, $R^2$, $R^3$, $R^4$, $R^5$ and $R^6$ are independently selected from hydrogen, $C_1-C_6$ alkyl, $C_1-C_6$ alkoxy, $C_1-C_6$ alkylthio, aryloxy, arylthio, amino, $C_1-C_6$ alkylamino, dialkylamino, phosphine, alkylphosphine, arylphosphine, halogen or the like, and at least one of $R^1$ to $R^6$ is bonded either directly or through a linking group to the substrate surface, e.g. through a linking group L as described in greater detail below. In certain embodiments, the diene moiety may be cyclic, where cyclopentadiene, oxazole and anthracene groups are exemplary

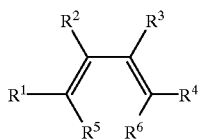

Where the cycloaddition reactive moiety is a dienophile group, the moiety is a group selected from: an alkene group; a moiety having a double bond between a carbon and a heteroatom; a moiety having a double bond between two heteroatoms, etc., where the moiety can undergo a [4+2] cycloaddition reaction with a suitable diene group, as described above. The dienophile group can be any group including, but not limited to, a substituted or unsubstituted alkene, or a substituted or unsubstituted alkyne. When the dienophile group is an alkene, it may be acyclic or cyclic (e.g., maleimide). In many embodiments, the dienophile group is a substituted alkene of the formula:

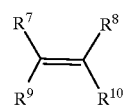

wherein $R^7$, $R^8$, $R^9$ and $R^{10}$ are independently selected from hydrogen, alkyl, e.g. lower alkyl ($C_1-C_6$ alkyl), formyl, acylamino, carboxy, alkoxycarbonyl, cyano, nitro, aryl, hydroxyalkyl, haloalkyl, aminoalkyl, cyanoalkyl, carboxyalkyl, halogen, alkylsulfonyl, trifluoromethyl or $C_2-C_6$ alkenyl and at least one of $R^7$ to $R^{10}$ is bonded either directly or through a linking group to the substrate, e.g. through a linking group as described infra.

Suitable cycloaddition reactive moieties that may be used in the subject methods are also described in WO 97/14706 and WO 98/30575, the disclosures of which are herein incorporated by reference. In certain preferred embodiments, the cycloaddition reactive moieties that are employed are not triazoline diones.

As mentioned above, the linker L may be a bond or linking group. Where L is a linking group, the choice of linker will depend on the nature of the polymer or substrate and whether it is desirable to detach the product from the polymer. Suitable linkers may include hydrocarbon chains, usually of 2 to 12 atoms, which structures may be linear or branched and include one or more features, e.g. annular structures, such as phenyl moieties, heteroatoms, e.g. N, S, O and the like.

The substrate or solid support having the surface characterized by the presence of cycloaddition reactive groups may be prepared using any convenient methodology. The particular methodology employed to prepare a given substrate surface for use in the subject methods necessarily depends on the nature of the substrate surface and the nature of the cycloaddition reactive group. For example, where the surface is a glass surface, conventional silanization procedures using silanizing agents, e.g. silyl, arylsilane, silyl ether etc., modified to include the cycloaddition reactive group (or have a reactivity moiety that is capable of reacting with a bonding to a cycloaddition reactive moiety in a manner that leaves the cycloaddition reactive moeity capable of participating in a cycloaddition reaction) may be employed. For example dienophile or diene modified alkyl siloxy compounds, e.g. 11-silyloxy-1-undecene, etc., may be employed. Alternatively, where the substrate is nylon, compounds comprising the cycloaddition reactive group and nylon reactive moiety, e.g. ammonium etc., may be employed to modify the surface of the nylon substrate.

For a representative protocol of how a substrate surface is prepared for use in the subject methods, see FIG. 1, which is further described infra.

Polymers

As summarized above, the subject invention provides methods for fabricating arrays of polymeric agents. The subject methods can be used to fabricate a number of different types of arrays in which a plurality of distinct polymeric binding agents are covalently attached with at least one surface of a substrate. The polymeric binding agents may vary widely, where the only limitation is that the polymeric binding agents are made up of two more, usually a plurality of, monomeric units covalently attached in sequential order to one another such that the polymeric compound has a sequence of monomeric units. Typically, the polymeric binding agent includes at least 5 monomeric units, usually at least 10 monomeric units and more usually at least 15 monomeric units, where in many embodiments the number of monomeric units in the polymers may be as high as 5000 or higher, but generally will not exceed about 2000. Polymeric binding agents of particular interest include biopolymeric molecules, such as peptides, nucleic acids, polysaccharides and the like, where peptides and nucleic acids, as well as synthetic mimetics thereof, are of particular interest in many embodiments.

In many embodiments, the polymeric binding agents present on the array surface are nucleic acids, including DNA, RNA, nucleic acids of one or more synthetic or non-naturally occurring nucleotides, and the like. The nucleic acids may be oligonucleotides, polynucleotides, including cDNAs, mRNAs, and the like. Where the polymeric compounds are nucleic acids, the nucleic acids will generally be at least about 5 nt, usually at least about 10 nt and more usually at least about 15 nt in length, where the nucleic acids may be as long as 5000 nt or longer, but generally will not exceed about 3000 nt in length and usually will not exceed about 2000 nt in length.

The polymers are characterized by comprising a cycloaddition reactive group, i.e. a moiety capable of participating in a cycloaddition reaction, at one position in the polymer, where in the broadest sense the cycloaddition reactive group may be positioned anywhere in the polymer. Generally, the cycloaddition reactive group will be positioned at one of the termini of the polymer, e.g. the 5' or 3' end of a nucleic acid. As such, in many embodiments of the subject invention, the polymers employed may be described by the following structure:

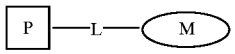

above; and

M is the cycloaddition reactive moiety, as described above, e.g. a diene or a dienophile moiety. The only limitation on the cycloaddition reactive group is that it be capable of reacting with the cycloaddition reactive group present on the substrate surface to produce a covalent linkage characterized by the presence of a cycloadduct, e.g. a six membered ring. Suitable cycloaddition reactive moieties that may be used in the subject methods are also described in WO 97/14706 and WO 98/30575, the disclosures of which are herein incorporated by reference. In certain preferred embodiments, the cycloaddition reactive moiety is not a triazoline dione.

The polymers employed in the subject methods may be prepared using any convenient methodology. The particular means of preparing the polymer to include the requisite cycloaddition reactive group will depend on the nature of the polymer and the nature of the cycloaddition reactive group which is to be incorporated into the polymer. For example, where the polymer is a peptide, a compound including the cycloaddition reactive moiety and a peptide reactive group, e.g. carboxy, hydroxy, phenoxy, amino, guanidino, thio, and the like, may be contacted with the peptide under conditions such that a conjugate is produced. Alternatively, where the polymer is a nucleic acid, a number of different protocols exist for producing a nucleic acid that includes a cycloaddition reactive group. For instance, the cycloaddition reactive group may be present on a modified phosphoramidite, which is covalently attached to the 5' terminus of a nucleic acid as the last step of a phosphoramidite synthesis. Alternatively, a modified nucleotide that includes a cycloaddition reactive group could be enzymatically added to one of the termini of a nucleic acid, e.g. a cycloaddition reactive group 3' modified 5' triphosphate nucleoside could be enzymatically added to the 3' end of a cDNA or a 5' modified nucleoside could be added to the 5' end of a cDNA.

For a representative protocol of how a polymer is prepared for use in the subject methods, see FIG. 1, which is further described infra.

Covalent Attachment

As mentioned above, in practicing the subject methods, at least two distinct polymers are contacted with the substrate surface. By distinct is meant that the two polymers differ from each other in terms of sequence of a monomeric units. The number of different polymers that are contacted with the substrate surface may vary depending on the desired nature of the array of the to be produced, i.e. the desired density of polymeric structures. Generally, the number of distinct polymers that are contacted with the surface of the array will be at least about 5, usually at least about 10 and more usually at least about 100, where the number may be as high as 1,000,000 or higher, but in many embodiments will not exceed about 500,000 and in certain embodiments will not exceed about 100,000.

Since the conditions under which the polymers are contacted with the surface are conditions sufficient for a cycloaddition reaction to occur, the polymers are generally contacted with the surface in an aqueous solvent, such that aqueous conditions are established at the surface location to which the polymer is to be covalently attached. The temperature during contact typically ranges from about 10 to 60 and usually from about 20 to 40° C. Following initial contact, the aqueous solution of polymer is typically maintained for a period of time sufficient for the desired amount of reaction to occur, where the period of time is typically at least about 20 sec, usually at least about 1 min and more usually at least about 10 min, where the period of time may be as great as 20 min or greater.

Each polymer is typically contacted with the substrate surface as part of an aqueous composition, i.e. an aqueous composition of the polymer in an aqueous solvent is contacted with the surface of the array. The aqueous solvent may be either water alone or water in combination with a co-solvent, e.g. an organic solvent, and the like. The aqueous composition may also contain one or more additional agents, including: acetic acid, monochloro acetic acid, dichloro acetic acid, trichloro acetic acid, acetonitrile, catalysts, e.g. lanthanide (III) trifluoromethylsulfate, lithium chloride, buffering agents, e.g. sodium phosphate, salts, metal cations, surfactants, enzymes, etc.

The aqueous polymer composition may be contacted with the surface using any convenient protocol. Generally, the aqueous polymer composition is contacted with the surface by depositing the aqueous polymer composition on the surface of the substrate. The aqueous volume may be deposited manually, e.g. via pipette, or through the use of an automated machine or device. A number of devices and protocols have been developed for depositing aqueous solutions onto precise locations of a support surface and may be employed in the present methods. Such devices include "ink-jet" printing devices, mechanical deposition or pipetting devices and the like. See e.g. U.S. Pat. Nos. 4,877,745; 5,338,688; 5,474,796; 5,449,754; 5,658,802; 5,700,637; and 5,807,552; the disclosures of which are herein incorporated by reference. Robotic devices for precisely depositing aqueous volumes onto discrete locations of a support surface, i.e. arrayers, are also commercially available from a number of vendors, including: Genetic Microsystems; Cartesian Technologies; Beecher Instruments; Genomic Solutions; and BioRobotics.

Because of the hydrophobic nature of the cycloaddition reactive group modified substrate surface, a large volume of fluid may be deposited into a drop that covers a relatively small are of the substrate surface. For example, volumes ranging from about 1 nl to 1 pl, usually from about 60 to 100 nl may be deposited onto the substrate surface and cover an relatively small area, e.g. will cover a spot having a diameter ranging from about 10 to 1000, usually from about 50 to 200 μm.

Following contact and incubation for a period of time and under conditions sufficient for cycloaddition reactions to occur between corresponding cycloaddition reactive moieties present on the polymers and substrate surface, as described above, the surface of the resultant array may be further processed as desired to in order to prepare the array for use, as described below. As such, the array surface may be washed to removed unbound reagent, e.g. unreacted polymer, and the like. Any convenient wash solution and protocol may be employed, e.g. flowing an aqueous wash solution, e.g. water, methanol, acetonitrile, and the like, across the surface of the array, etc. The surface may also be dried and stored for subsequent use, etc.

A representative embodiment of the covalent attachment of an oligonucleotide to the surface of a substrate is now described with reference to FIG. 1. In FIG. 1, a diene conjugated to an oligonucleotide is reactive with a dienophile covalently attached to a glass surface. In preparing the diene modified oligonucleotide, a diene 1 is modified with β-cyanoethyl phosphoramidite to yield the phosphoramidite derivative 2. The phosphoramidite derivative of the diene is then coupled to an oligonucleotide having a free 5'-hydroxyl group, first forming a phosphite product, which is oxidized to afford the corresponding phosphate ester 3.

To prepare the glass surface, a dienophile 5 is covalently attached to the glass surface in two steps. First, the glass surface is modified to incorporate a linker with a reactive group Z, where Z is an amine, hydroxyl, cyano, hydrazide or sulfhydryl group, or the like. The reactive group Z on the modified surface 4 is then reacted with a complementary functional group $R^9$, such as an amine or carboxyl group, on the dienophile 5.

Following preparation of the substrate surface and modified oligonucucleotide, the substrate surface 6 is treated with an aqueous solution of the oligonucleotide-diene conjugate 3. Diels-Alder reaction of the cycloaddition-reactive moieties present on the substrate surface and the oligonucleotide produces the surface 7, having the oligonucleotide immobilized on the glass surface.

Arrays

Also provided by the subject invention are novel arrays of polymeric binding agents. The subject arrays include at least two distinct polymers that differ by monomeric sequence covalently attached to different and known locations on the substrate surface. Each distinct polymeric sequence of the array is typically present as a composition of multiple copies of the polymer on the substrate surface, e.g. as a spot on the surface of the substrate. The number of distinct polymeric sequences, and hence spots or similar structures, present on the array may vary, but is generally at least 2, usually at least 5 and more usually at least 10, where the number of different spots on the array may be as a high as 50, 100, 500, 1000, 10,000 or higher, depending on the intended use of the array. The spots of distinct polymers present on the array surface are generally present as a pattern, where the pattern may be in the form of organized rows and columns of spots, e.g. a grid of spots, across the substrate surface, a series of curvilinear rows across the substrate surface, e.g. a series of concentric circles or semi-circles of spots, and the like. The density of spots present on the array surface may vary, but will generally be at least about 10 and usually at least about 100 spots/cm$^2$, where the density may be as high as 10$^6$ or higher, but will generally not exceed about 10$^5$ spots/cm$^2$.

A critical aspect of the subject arrays is that at least a portion of, generally at least 50 number %, usually at least 60 number % and more usually at least 75 number %, of the polymers present on the array surface are covalently attached to the surface through a linking group that includes a cycloadduct. The cycloadduct may be a 4n to 4n+2 (where n:1,2,3,4) membered ring structure, where the ring structure may be a heteroannular structure. In many embodiments, the cycloadduct is a six membered ring, which may or may not include one or more heteroannular atoms, where heteroannular atoms that may be present include N, S, O, etc. In many embodiments, the cycloadduct is a cycloalkyl structure, e.g. cyclohexene.

In addition to the cycloadduct, the linking group is further characterized in being from about 1 to 50 long, usually from about 1 to 5 methylenes long, where the linking group may be characterized by the presence of saturated or unsaturated alkyl chains, annular structures, e.g. phenyl groups, heteroatoms, including N, O, S etc., and the like.

Because of the presence of the cycloreactive moiety on the surface of the substrate used to prepare the subject arrays, the subject arrays are further characterized in that the spots present on the array surface may be small (due to lack of spreading of the deposited aqueous solution on the array surface during preparation). By small is meant that each spot on the array has a diameter that is at least about 1 μm, usually at least about 5 μm and more usually at least about 10 μm and does not exceed about 1 mm, usually does not exceed about 500 μm and more usually does not exceed about 200 μm. Despite the relatively small size of the spot, a relatively large amount of nucleic acid may be present in each spot, where the amount may range from about 0.01 to 1.0 mg/ml, usually from about 0.1 to 0.5 mg/ml.

In the broadest sense, the arrays of the subject invention are arrays of polymeric binding agents, where the polymeric binding agents may be any of: peptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini, e.g. the 3' or 5' terminus.

Utility

The subject arrays find use in a variety applications, where such applications are generally analyte detection applications in which the presence of a particular analyte in a given sample is detected at least qualitatively, if not quantitatively. Protocols for carrying out such assays are well known to those of skill in the art and need not be described in great detail here. Generally, the sample suspected of comprising the analyte of interest is contacted with an array produced according to the subject methods under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g. through use of a signal production system, e.g. an isotopic or fluorescent label present on the analyte, etc. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g. a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. Patents and patent applications describing methods of using arrays in various applications include: U.S. Pat. No. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; WO 95/21265; WO 96/31622; WO 97/10365; WO 97/27317; EP 373 203; and EP 785 280; the disclosures of which are herein incorporated by reference.

Kits

Finally, kits for use in analyte detection assays are provided. The subject kits at least include the arrays of the subject invention. The kits may further include one or more additional components necessary for carrying out the analyte detection assay, such as sample preparation reagents, buffers, labels, and the like. In addition, the kits typically further include instructions for how practice the subject analyte detection methods according to the subject invention, where these instructions are generally present on at least one of a package insert and the package of the kit.

The following is offered by way of illustration and not by way of limitation.

Experimental

I. Surface Preparation

A. Diene on Surface

1. Silylating Agent Preparation

A concentrated solution of tetrachlorosilane in toluene is stirred at 0° C., a solution of 2,4-hexadien-1-ol in toluene is added dropwise. After total addition, the temperature is allowed to return to room temperature. After 1 hour the solution is evaporated under vacuum, then the remaining liquid is distilled under vacuum.

2. Silylation

Glass slides are washed in nitric acid for 10 minutes, then wash with water. The slides are cured in oven at 150° C. for 4 hours, then they are put in a glass reactor where a 1% solution of the silylating agent in toluene is added. The reaction is left at 90° C. for 4 hours. After that the solution is removed and the slide are wash with dry toluene. After 2 washes the slide are removed from the reactor and cured at 150° C. for 2 hours B. Dienophile on Surface 1. Silylating Agent Preparation A solution of 1-bromo-10-undecenyl in ether with magnesium is stirred. After completion of the synthesis of the magnesian product, tetrachlorosilane is added dropwise with an addition funnel. After 2 hours, the solution is evaporated under vacuum. Then the resulting oil-solid is distilled under vacuum to give the resulting silylating agent as a liquid.

2. Silylation

As above

II. DNA Preparation

A. Phosphoramidite Synthesis

Procedures analogous to thos disclosed in WO 98/30575, p28 and U.S. patent application Ser. No. 08/264,029, the disclosures of which are incorporated by reference are employed. A phosphoramidite with a dienophile is coupled during the synthesis, or at the end of the synthesis. Or a solid support loaded with a modified first nucleoside is used.

B. Enzymatic Ligation Nucleoside Preparation

Procedures analogous to those described in WO 98/30575 p 62 and J.Org.Chem 1989, 54, 631–635, the disclosures of which are herein incorporated by reference, are employed.

III. DNA Loading

The oligonucleotide in solution in an aqueous phosphate buffer at pH 6.8 and room temperature is deposited on the DNA array. The DNA array is in a chamber with a moisture saturated atmosphere. After 15 minutes the array is washed and ready for hybridization.

It is evident from the above results and discussion that an important new protocol for preparing polymeric arrays, particularly nucleic acid arrays, is provided by the subject invention. With respect to nucleic acid arrays, the subject methods provide a means for covalently attaching nucleic acids to a substrate surface in which a crosslinker is not employed, reaction of nucleobases need not occur and the reaction may be carried out in an aqueous environment. Furthermore, the nature of the surface of the substrates employed in the subject methods limits fluid spreading during deposition, allowing the production of small nucleic acid spots on the surface of the substrate. In addition, the subject methods allow one to synthesize the nucleic acids apart from the substrate, e.g. using conventional synthesis procedures, then specifically attach the nucleic acids to the support surface at either their 3' or 5' terminus. As such, the subject arrays can be produced while enjoying the benefits of conventional solid phase nucleic acid synthesis, such as high yield and excellent purity. Accordingly, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of making an array of at least two distinct polymeric compounds of differing composition covalently bonded to a surface of a solid support, said method comprising:

contacting a surface of a solid support having a cycloaddition reactive group and a contact angle ranging from about 20° to 100° with said distinct polymeric compounds under conditions sufficient for said polymeric compounds to covalently bond to said surface by a cycloaddition reaction.

2. The method according to claim 1, wherein said cycloaddition reaction comprises the reaction of a diene with a dienophile.

3. The method according to claim 1, wherein said cycloaddition reaction produces a six membered ring between said polymers and said surface.

4. The method according to claim 1, wherein said polymers are nucleic acids.

5. A method of producing an array of at least two distinct nucleic acids that differ by sequence covalently bonded to the surface of a solid support, said method comprising:
  contacting a surface of a solid support having a cycloaddition reactive group and a contact angle ranging from about 20 to 100° with said nucleic acids under conditions sufficient for said nucleic acids to covalently bond to said surface by a Diels-Alder reaction;
  whereby said array of nucleic acids is produced.

6. The method according to claim 5, wherein a terminus of said nucleic acids comprises diene and said surface comprises a dienophile.

7. The method according to claim 5, wherein a terminus of said nucleic acids comprises a dienophile and said surface comprises a diene.

8. The method according to claim 5, wherein said dienophile comprises a double bond.

9. The method according to claim 5, wherein said nucleic acid is a polydeoxyribonucleotide.

10. A method of producing an array of at least two distinct polydeoxyribonucleotides that differ by sequence covalently bonded to the surface of a solid support, said method comprising:
  contacting a surface of a solid support having a cycloaddition reactive group and a contact angle ranging from about 20 to 100° with said polydeoxyribonulcucleotides under conditions sufficient for said nucleic acids to covalently bond to said surface by a Diels-Alder reaction, wherein a terminus of said polydeoxyribonucleotides comprises a diene and said surface comprises a dienophile;
  whereby said array of nucleic acids is produced.

11. The method according to claim 10, wherein said contacting comprises depositing an aqueous composition of said polydeoxyribonucleotides onto said surface.

12. The method according to claim 11, wherein said depositing is by a drop deposition device.

13. The method according to claim 11, wherein said depositing is by an ink jet device.

14. A method of making a polymeric array of at least: (a) a first spot having a diameter ranging from 10 to 1000 μm and made up of a first polymer covalently bound to a surface; and (b) a second spot having a diameter ranging from 10 to 1000 μm and made up of a second polymer covalently bound to said surface of said solid support; said method comprising:
  depositing:
    (a) from about 1 nl to 1 pl of a first fluid composition comprising said first polymer onto a surface having a cycloaddition reactive group and a contact angle ranging from about 20 to 100° to produce said first spot having a diameter ranging from 10 to 1000 μm; and
    (b) from about 1 nl to 1 pl of a second fluid comprising said second polymer onto said surface to produce said second spot having a diameter ranging from 10 to 1000 μm,
  wherein said first and second fluid compositions are deposited onto said surface under conditions sufficient for said first and second polymeric compounds to covalently bond to said surface by a cycloaddition reaction;
  whereby said polymeric array is produced.

15. The method according to claim 14, wherein said cycloaddition reaction comprises the reaction of a diene with dienophile.

16. The method according to claim 14, wherein said cycloaddition reaction produces a six membered ring between said first and second polymers and said surface.

17. The method according to claim 14, wherein said polymers are nucleic acids.

18. A method of making a nucleic acid array of at least: (a) a first spot having a diameter ranging from 10 to 1000 μm and made up of a first nucleic acid covalently bound to a surface; and (b) a second spot having a diameter ranging from 10 to 1000 μm and made up of a second nucleic acid covalently bound to said surface of said solid support; said method comprising:
  depositing:
    (a) from about 1 nl to 1 pl of a first fluid composition comprising said first nucleic acid onto a surface having a cycloaddition reactive group and a contact angle ranging from about 20 to 100° to produce said first spot having a diameter ranging from 10 to 1000 μm; and
    (b) from about 1 nl to 1 pl of a second fluid comprising said second nucleic acid onto said surface to produce said second spot having a diameter ranging from 10 to 1000 μm,
  wherein said first and second fluid compositions are deposited onto said surface under conditions sufficient for said first and second nucleic acids to covalently bond to said surface by Diels-Alder reaction:
  whereby said array of nucleic acids is produced.

19. The method according to claim 18, wherein a terminus of each of said first and second nucleic acids comprises diene and said surface comprises a dienophile.

20. The method according to claim 19, wherein said dienophile comprises a double bond.

21. The method according to claim 18, wherein a terminus of each of said nucleic acids comprises a dienophile and said surface comprises a diene.

22. The method according to claim 21, wherein said dienophile comprises a double bond.

23. The method according to claim 18, wherein said nucleic acids are polydeoxyribonucleotides.

24. A method of making a polydeoxyribonucleotide array of at least: (a) a first spot having a diameter ranging from 10 to 1000 μm and made up of a first polydeoxyribonucleotide covalently bound to a surface; and (b) a second spot having a diameter ranging from 10 to 1000 μm and made up of a second polydeoxyribonucleotide covalently bound to said surface of said solid support; said method comprising:
  depositing:
    (a) from about 1 nl to 1 pl of a first fluid composition comprising said first polydeoxyribonucleotide onto a surface having a cycloaddition reactive group and a contact angle ranging from about 20 to 100° to produce said first spot having a diameter ranging from 10 to 1000 μm; and
    (b) from about 1 nl to 1 pl of a second fluid comprising said second polydeoxyribonucleotide onto said surface to produce said second spot having a diameter ranging from 10 to 1000 μm,
  wherein said first and second fluid compositions are deposited onto said surface under conditions sufficient for said first and second polydeoxyribonucleotide to covalently bond to said surface by a Diels-Alder reaction;
  whereby said array of polydeoxyribonucleotides is produced.

25. The method according to claim 24, wherein a terminus of each of said first a second polydeoxyribonucleotides comprises a diene and said surface comprises a dienophile.

26. The method according to claim 24, wherein a terminus of each of said first a second polydeoxyribonucleotides comprises a dienophile and said surface comprises a diene.

27. The method according to claim 24, wherein said depositing is by a drop deposition device.

28. The method according to claim 24, wherein said depositing is by an ink jet device.

29. The method according to claim 1 wherein the contact angle ranges from about 40 to 100°.

30. The method according to claim 10 wherein the contact angle ranges from about 40 to 100°.

31. The method according to claim 14 wherein the contact angle ranges from about 60 to 100°.

32. The method according to claim 24 wherein the contact angle ranges from about 40 to 100°.

* * * * *